United States Patent [19]

Evans et al.

[11] Patent Number: 5,488,188
[45] Date of Patent: Jan. 30, 1996

[54] PROCESS FOR THE PREPARATION OF (E)-1-AMINO-2-(FLUOROMETHYLENE)-4-(P-FLUOROPHENYL)BUTANE, PROCESSES FOR PREPARING AN INTERMEDIATE THEREOF, AND INTERMEDIATES THEREOF

[75] Inventors: Jonathan C. Evans; Christian T. Goralski, both of Midland; Cynthia L. Rand, Sanford; Paul C. Vosejpka, Midland, all of Mich.

[73] Assignee: Merrell Dow Pharmaceuticals Inc., Cincinnati, Ohio

[21] Appl. No.: 315,041

[22] Filed: Sep. 29, 1994

[51] Int. Cl.[6] ............ C07C 25/13; C07C 19/08; C07C 21/18
[52] U.S. Cl. ............ 570/128.000; 570/124.000; 570/127.000; 570/134.000; 570/135.000
[58] Field of Search ............ 570/127, 128, 570/134, 135, 124

[56] References Cited

U.S. PATENT DOCUMENTS

| | | | |
|---|---|---|---|
| 3,852,366 | 12/1974 | Bechtold et al. | 570/127 |
| 4,454,159 | 6/1984 | Bey | 424/330 |

FOREIGN PATENT DOCUMENTS

| | | | |
|---|---|---|---|
| 649772 | 10/1962 | Canada | 570/127 |
| 0066943 | 12/1982 | European Pat. Off. | 570/128 |
| 0295604 | 12/1988 | European Pat. Off. | |
| 9324120 | 12/1993 | WIPO | |

OTHER PUBLICATIONS

Allenstein, Eckhard, et al., *Chemische Berichte*, vol. 100, pp. 3551–3563 (1967)—English translation.
McCloskey Allen L., et al., *Organic Syntheses*, vol. IV, pp. 261–266 (1963).
Rakshit, Jitendra Nath, *Jour. of the Chemical Society*, vol. 103, pp. 1557–1562 (1913).
Yinglin, Han, et al., *Synthesis*, No. 2, Feb. 1990, pp. 122–124.
Yinglin, Han, et al., *Synthesis*, No. 7, Jul. 1990, pp. 615–618.

*Primary Examiner*—Werren B. Lone
*Attorney, Agent, or Firm*—Charlotte L. Barney

[57] ABSTRACT

The present invention relates to a novel process for preparing (E)-1-amino-2-(fluoromethylene)-4-(p-fluorophenyl)butane, also known in the art as (E)-(p-fluorophenethyl)-3-fluoroallylamine, novel intermediates thereof, a novel process for the preparing (E)-2-(fluoromethylene)-4-(p-fluorophenyl)butan-1-ol, and a novel process for preparing alkali metal salts of diformylamide.

2 Claims, No Drawings

PROCESS FOR THE PREPARATION OF (E)-1-AMINO-2-(FLUOROMETHYLENE)-4-(P-FLUOROPHENYL)BUTANE, PROCESSES FOR PREPARING AN INTERMEDIATE THEREOF, AND INTERMEDIATES THEREOF

The present invention relates to a novel process for preparing (E)-1-amino-2-(fluoromethylene)-4-(p-fluorophenyl)butane, also known in the art as (E)-(p-fluorophenethyl)-3-fluoroallylamine, and pharmaceutically acceptable salts thereof, which are useful as irreversible inhibitors of monoamine oxidase U.S. Pat. No. 4,454,158, Jun. 12, 1984, to novel processes for the preparation of an intermediate thereof, and to novel intermediates useful in the preparation of (E)-1-amino-2-(fluoromethylene)-4-(p-fluorophenyl)butane.

BACKGROUND OF THE INVENTION

A general process for preparing allyl amines including (E)-1-amino-2-(fluoromethylene)-4-(p-fluorophenyl)butane is described in U.S. Pat. No. 4,454,158, issued Jun. 12, 1984. A process for preparing (E)-1-amino-2-(fluoromethylene)-4-(p-fluorophenyl)butane is described in International Application No. WO 93/24120, (PCT) published Dec. 9, 1993 and European Pat. Application No. 0 295 604, published Dec. 21, 1988.

These methods, however, have the disadvantage that some of the steps to prepare a useful intermediate, (E)-2-(fluoromethylene)- 4-(p-fluorophenyl)butan-1-ol, use reagents and conditions that do not allow for economical, large scale, production of (E)-2-(fluoromethylene)-4-(p-fluorophenyl)butan- 1-ol. Further, these methods use a phthalimide containing intermediate, the removal of which gives (E)-1-amino-2-(fluoromethylene)-4-(p-fluorophenyl)butane contaminated with phthalhydrazide which is difficult to remove from the final product.

The process of the present invention for preparing (E)-1-amino-2-(fluoromethylene)-4-(p-fluorophenyl)butane utilizes alkali metal salts of diformylamide. Generally, these salts are only partially soluble in useful solvents which causes the reaction rate to be surface area dependent.

The preparation and use of alkali metal salts of diformylamide is known in the art. J. N. Rakshit, *J. Chem. Soc.*, 103, 1557–1562 (1913); E. Allenstein and V. Beyl, *Chem. Ber.* 100, 3551–3563 (1967); H. Yinglin and H. Hongwen, *Synthesis* 7, 122–124 (1990); and H. Yinglin and H. Hongwen, *Synthesis* 7, 615–618 (1990).

The methods for preparing alkali metal salts of diformylamide, however, have the disadvantage that the material is obtained as a solid mass. The solid obtained must be broken up which leads to material of differing and irregular particle size. Moreover, milling alkali metal salts of diformylamide to increase the surface area creates dust and inhalation problems. Further, the method of E. Allenstein and V. Beyl for preparing alkali metal salts of diformylamide, when carried out on large scale, gives material that is contaminated with detrimental amounts of methanol and ammonia.

An object of the present invention, therefore, is to provide novel methods for the economical preparation of (E)-2-(fluoromethylene)-4-(p-fluorophenyl)butan-1-ol which can be carried out without purification between steps.

Another object of the present invention is to provide a novel method for producing (E)-1-amino-2-(fluoromethylene)-4-(p-fluorophenyl)butane utilizing intermediates which provide the final product without difficult to remove by-products.

Another object of the present invention is to provide a novel process for crystallizing alkali metal salts of diformylamide that gives alkali metal salts of diformylamide as a free flowing granular solid that is free of detrimental amounts of methanol and ammonia.

A further object of the present invention is to provide novel intermediates useful for preparing (E)-1-amino-2-(fluoromethylene)- 4-(p-fluorophenyl)butane.

SUMMARY OF THE INVENTION

The present invention provides a novel process for preparing (E)-2-(fluoromethylene)-4-(p-fluorophenyl)butan-1-ol comprising the steps of:

a) reacting 4-(p-fluorophenyl)butyric acid with isobutylene to give t-butyl 4-(p-fluorophenyl)butyrate;

b) reacting t-butyl 4-(p-fluorophenyl)butyrate with an appropriate alkyl chloroformate to give an alkyl 2-(t-butoxycarbonyl)- 4-(p-fluorophenyl)butyrate;

c) reacting an alkyl 2-(t-butoxycarbonyl)-4-(p-fluorophenyl)butyrate with an appropriate difluoromethane transfer reagent to give an alkyl 2-(difluoromethyl)-2-t-butoxycarbonyl- 4-(p-fluorophenyl)butyrate:

d) reacting an alkyl 2-(difluoromethyl)-2-(t-butoxycarbonyl)- 4-(p-fluorophenyl)butyrate with an appropriate acid to give an alkyl 2-(difluoromethyl)-2-carboxy- 4-(p-fluorophenyl)butyrate;

e) reacting an alkyl 2-(difluoromethyl)-2-carboxy-4-(p-fluorophenyl)butyrate with an appropriate base to give an alkyl (E)-2-(fluoromethylene)-4-(p-fluorophenyl)butyrate;

f) reacting an alkyl (E)-2-(fluoromethylene)-4-(p-fluorophenyl)butyrate with an appropriate reducing agent.

Furhter, the present invention provides a novel process for preparing (E)-2-(fluoromethylene)-4-(p-fluorophenyl)butan- 1-ol comprising the steps of:

a) reacting 4-(p-fluorophenyl)butyric acid with isobutylene to give t-butyl 4-(p-fluorophenyl)butyrate;

b) reacting t-butyl 4-(p-fluorophenyl)butyrate with an appropriate alkyl chloroformate to give a reaction mixture and then reacting the reaction mixture with an appropriate difluoromethane transfer reagent to give an alkyl 2-(difluoromethyl)- 2-(t-butoxycarbonyl)-4-(p-fluorophenyl)butyrate;

c) reacting an alkyl 2-(difluoromethyl)-2-(t-butoxycarbonyl)- 4-(p-fluorophenyl)butyrate with an appropriate acid to give an alkyl 2-(difluoromethyl)-2-carboxy- 4-(p-fluorophenyl)butyrate;

d) reacting an alkyl 2-(difluoromethyl)-2-carboxy-4-(p-fluorophenyl)butyrate with an appropriate base to give an alkyl (E)-2-(fluoromethylene)-4-(p-fluorophenyl)butyrate;

e) reacting an alkyl (E)-2-(fluoromethylene)-4-(p-fluorophenyl)butyrate with an appropriate reducing agent.

In addition, the present invention provides a novel process for preparing (E)-1-amino-2-(fluoromethylene)-4-(p-fluorophenyl)butane and pharmaceutically acceptable salts thereof comprising the steps of:

a) reacting (E)-2-(fluoromethylene)-4-(p-fluorophenyl)butan- 1-ol with an appropriate halogenating agent to give a (E)-1-halo-2-(fluoromethylene)-4-(p-fluorophenyl)butane;

b) reacting a (E)-1-halo-2-(fluoromethylene)-4-(p-fluorophenyl)butane with an alkali metal salt of diformylamide to give (E)-N-(2-(fluoromethylene)-4-(p-fluorophenyl)butyl)-N-formyl formamide;

c) reacting (E)-N-(2-(fluoromethylene)-4-(p-fluorophenyl)butyl)-N-formyl formamide with an appropriate hydrolysis agent.

In addition, the present invention provides a novel process for crystallizing alkali metal salts of diformylamide comprising the steps of:
a) dissolving an alkali metal salt of diformylamide in a hydroxylic solvent;
b) distilling the hydroxylic solvent while adding an antisolvent.

In addition, the present invention provides for novel compounds of the formula:

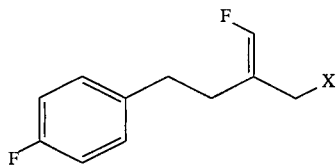

wherein

X is chloro, bromo or —N(CHO)$_2$.

DETAILED DESCRIPTION OF THE INVENTION

As used in this application:
a) the term "—N(CHO)$_2$" refers to a radical of the formula;

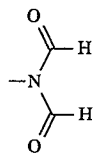

b) the term "halo" refers to a chlorine atom, a bromine atom, or an iodine atom;
c) the term "pharmaceutically acceptable salts" refers to acid addition salts.

The expression "pharmaceutically acceptable acid addition salts" is intended to apply to any non-toxic organic or inorganic acid addition salt of (E)-1-amino-2-(fluoromethylene)- 4-(p-fluorophenyl)butane. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as p-toluenesulfonic acid, methanesulfonic acid and 2-hydroxyethanesulfonic acid. Such salts can exist in either a hydrated or substantially anhydrous form.

Examples of compounds encompassed by the present invention include:

(E)-1-chloro-2-(fluoromethylene)-4-(p-fluorophenyl)butane;

(E)-1-bromo-2-(fluoromethylene)-4-(p-fluorophenyl)butane;

(E)-N-(2-(fluoromethylene)-4-(p-fluorophenyl)butyl)-N-formyl formamide.

A general synthetic procedure is set forth in Scheme A. In Scheme A, all substituents unless otherwise indicated, are as previously defined. Reagents, techniques, and procedures used in Scheme A are well known and appreciated by one of ordinary skill in the art.

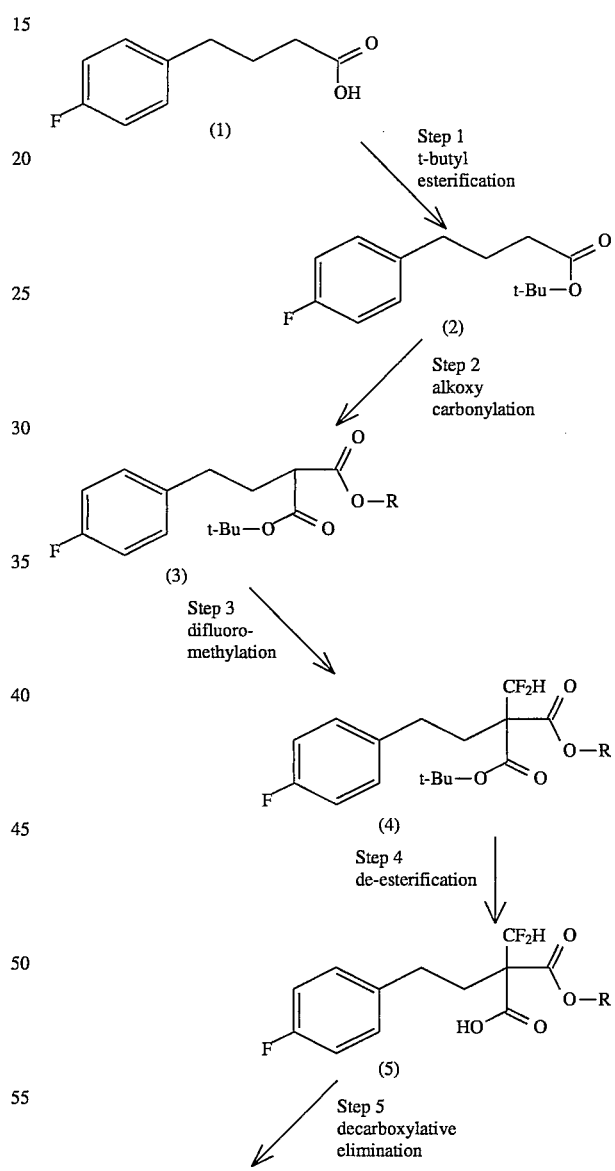

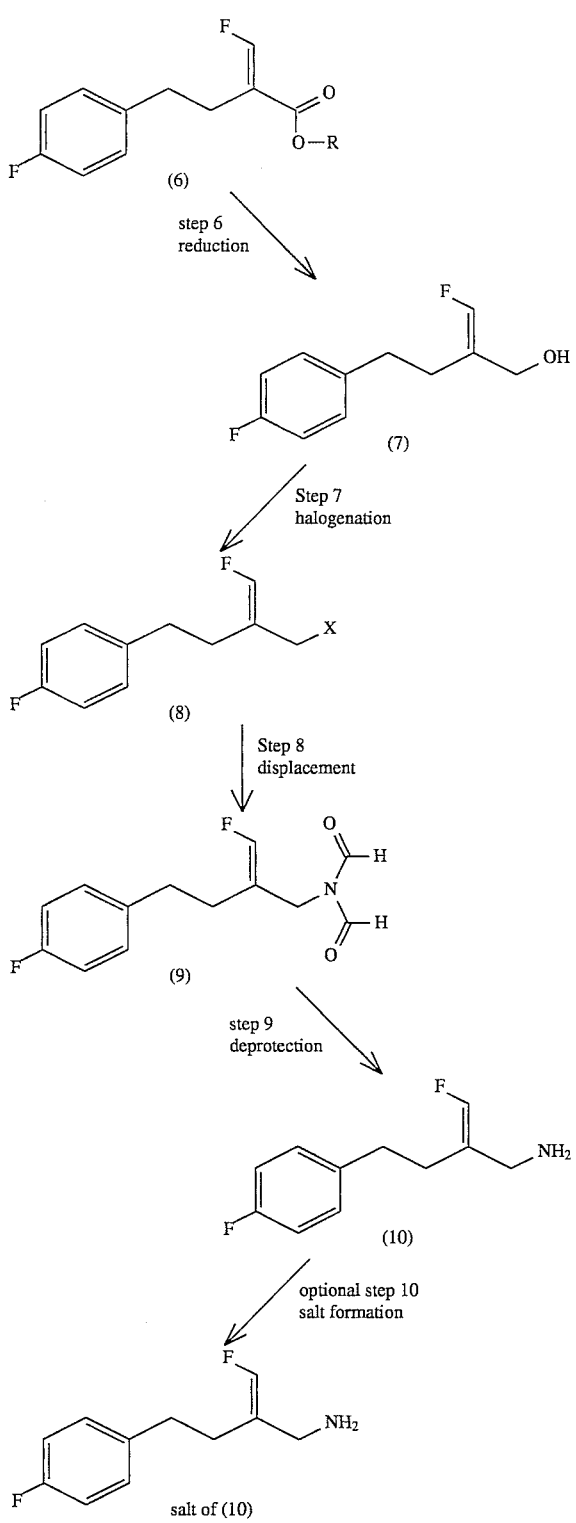

-continued
SCHEME A preferred. The reaction is tolerant of some water in the starting material with the use of 4-(p-fluorophenyl)butyric acid containing less than 5% by weight water being preferred. The reaction is carried out in isobutylene without a solvent. The reaction is carried out using 1 to about 5 molar equivalents of isobutylene, with 2 to 4 molar equivalents being preferred and 3 molar equivalents being most preferred. The reaction can be carried out by combining 4-(p-fluorophenyl)butyric acid and a strong acid catalyst and either adding the resulting mixture to isobutylene or preferably adding isobutylene to the resulting mixture. Regardless of the order of addition, cooling is required to control the exotherm that occurs during mixing. When isobutylene is added to a 4-(p-fluorophenyl)butyric acid/sulfuric acid mixture, the mixture is cooled to a temperature of between −30° C. and 0° C. before the addition of isobutylene, with −20° C. and −10° C. being preferred. The reaction is carried out at a temperature of from about 0° C. to about 40° C, with 10° C. to 30° C. being preferred and 20° C. to 25° C. being most preferred. The reaction generally requires from 3 to 12 hours. The product is obtained by quenching with a suitable base, such as sodium hydroxide or potassium hydroxide, in the presence of isobutylene. The quench is carried out at a temperature of from about −5° C. to about 5° C. The product can be used after isolation by methods well known and appreciated in the art, such as extraction and evaporation. The product can be purified by methods well known and appreciated in the art, such as distillation.

In Scheme A, step 2, t-butyl 4-(p-fluorophenyl)butyrate is contacted with an appropriate alkyl chloroformate to give an alkyl 2-(t-butoxycarbonyl)-4-(p-fluorophenyl)butyrate.

An appropriate alkyl chloroformate is one which transfers an alkoxy carbonyl group which allows for selective removal of the t-butyl ester, does not interfere with the difluoromethylation step or the decarboxylative elimination step and can be subsequently reduced to give a hydroxymethyl group. Examples of an appropriate alkyl chloroformate include methyl chloroformate, ethyl chloroformate, propyl chloroformate, butyl chloroformate, isobutyl chloroformate, and the like, with ethyl chloroformate being preferred.

For example, t-butyl 4-(p-fluorophenyl)butyrate is contacted with an appropriate alkyl chloroformate. The reaction is carried out in a suitable solvent such as tetrahydrofuran, or toluene/tetrahydrofuran mixtures. The reaction is carried out using from about 1 to about 2 molar equivalents of a suitable base. A suitable base is non-nucleophilic and is of sufficient strength to remove a proton from the methylene moiety adjacent to the carboxy group of the starting ester. Suitable bases are known in the art, and include sodium hydride, sodium bis(trimethylsilyl)amide, lithium diisopropylamide, and the like. The reaction is carried out at a temperature of from about −78° C. to about 0° C., with −20° C. 0° C. to being preferred. The formation of by-products is minimized by the addition of t-butyl 4-(p-fluorophenyl)butyrate to a solution of a suitable base followed by addition of an appropriate alkyl chloroformate. The product can be isolated by methods well known and appreciated in the art, such as extraction and evaporation. The product can be purified by methods well known and appreciated in the art, such as chromatography and distillation.

In Scheme A, step 3, an alkyl 2-(t-butoxycarbonyl)-4-(p-fluorophenyl)butyrate is contacted with an appropriate difluoromethane transfer reagent to give an alkyl 2-(difluoromethyl)- 2-(t-butoxycarbonyl)-4-(p-fluorophenyl)butyrate.

An appropriate difluoromethane transfer reagent is one that transfers a difluoromethyl group under the conditions of the reaction. Examples of an appropriate difluoromethane In Scheme A, step 1, 4-(p-fluorophenyl)butyric acid is contacted with isobutylene to give t-butyl 4-(p-fluorophenyl)butyrate.

For example, 4-(p-fluorophenyl)butyric acid is contacted with isobutylene. The reaction is carried out using 5% to 15% by weight of a strong acid catalyst, such as sulfuric acid, with 8% to 12% being preferred and 10% being most transfer reagent include chlorodifluoromethane, bromodifluoromethane, and the like.

For example, an alkyl 2-(t-butoxycarbonyl)-4-(p-fluorophenyl)butyrate is contacted with from 1.25 to 1.4 molar equivalents of an appropriate difluoromethane transfer reagent. The reaction is carried out in a suitable solvent, such as tetrahydrofuran, or toluene/tetrahydrofuran mixtures. The reaction is carried out using a suitable base. A suitable base is non-nucleophilic and is of sufficient strength to remove a proton from the methine moiety adjacent to the carboxy groups of the starting diester. Suitable bases having a sodium counter ion being preferred. Suitable bases are known in the art, and include sodium hydride, sodium t-butoxide and sodium bis(trimethylsilyl)amide, with sodium bis(trimethylsilyl)amide being preferred and sodium bis(trimethylsilyl)amide having a titration value of 2.1 or less being most preferred. The reaction is carried out at a temperature of from about 20° C. to about 50° C., with 40° C. to 45° C. being preferred. The reaction generally requires 30 minutes to 2 hours. The product is obtained by quenching using a suitable acid, such as acetic acid. The quench is carried out at a temperature of from about 15° C. to about 25° C. The product can be isolated by extraction and used as a solution without purification or the product can be obtained as a solution in another solvent by exchanging solvents by evaporation, as is well known in the art. The product can be isolated and purified by methods well known and appreciated in the art, such as extraction, evaporation, and distillation.

In Scheme A, step 2 and step 3 can be carried out without isolating the compound of structure (3) formed in step 2, thus, a t-butyl 4-(p-fluorophenyl)butyrate is contacted with an appropriate alkyl chloroformate to give a reaction mixture and then the reaction mixture is contacted with an appropriate difluoromethane transfer reagent to give an alkyl 2-(difluoromethyl)-2-(t-butoxycarbonyl)-4-(p-fluorophenyl)butyrate.

An appropriate alkyl chloroformate is as defined in Scheme A, step 2, and an appropriate difluoromethane transfer reagent is as defined in Scheme A, step 3.

For example, t-butyl 4-(p-fluorophenyl)butyrate is contacted with an appropriate alkyl chloroformate. The reaction is carried out in a suitable solvent such as tetrahydrofuran, or toluene/tetrahydrofuran mixtures. The reaction is carried out using from about 2 to about 3 molar equivalents of a suitable base. A suitable base is non-nucleophilic and is of sufficient strength to remove a proton from the methylene moiety adjacent to the carboxy group of the starting ester. Suitable bases having a sodium counter ion being preferred. Suitable bases are known in the art, and include sodium hydride, sodium t-butoxide and sodium bis(trimethylsilyl)amide, with sodium bis(trimethylsilyl)amide being preferred and sodium bis(trimethylsilyl)amide having a titration value of 2.1 or less being most preferred. The reaction with an appropriate alkyl chloroformate is carried out at a temperature of from about −70° C. to about 0° C., with −20° C. to 0° C. being preferred. The formation of by-products is minimized by the addition of t-butyl 4-(p-fluorophenyl)butyrate to a solution of a suitable base followed by addition of an appropriate alkyl chloroformate.

After a time, generally, 10 minutes to 3 hours, a reaction mixture is obtained which comprises a substantial amount of an alkyl 2-(t-butoxycarbonyl)-4-(p-fluorophenyl)butyrate, along with the selected suitable base, as a solution in the selected suitable solvent. The reaction mixture is warmed to a temperature of from about 20° C. to about 50° C., with 40° C. to 45° C. being preferred. The reaction mixture is then contacted with from 1.25 to 1.4 molar equivalents of an appropriate difluoromethane transfer reagent. Generally, the reaction with an appropriate difluoromethane transfer reagent requires 30 minutes to 2 hours. The product is obtained by quenching using a suitable acid, such as acetic acid. The quench is carried out at a temperature of from about 15° C. to about 25° C. The product can be isolated by extraction and used as a solution without purification or the product can be obtained as a solution in another solvent by exchanging solvents by evaporation, as is well known in the art. The product can be isolated and purified by methods well known and appreciated in the art, such as extraction, evaporation, and distillation.

In Scheme A, step 4, an alkyl 2-(difluoromethyl)-2-(t-butoxycarbonyl)- 4-(p-fluorophenyl)butyrate with an appropriate acid to give an alkyl 2-(difluoromethyl)-2-carboxy-4-(p-fluorophenyl)butyrate.

For example, an alkyl 2-(difluoromethyl)-2-(t-butoxycarbonyl)- 4-(p-fluorophenyl)butyrate is contacted with 5% to 30% by weight of an appropriate acid. An appropriate acid is an organic or inorganic acid which serves as a catalyst for the removal of a t-butyl ester but does not cause the formation of detrimental by-products. Examples of an appropriate acid include trifluoroacetic acid, methanesulfonic acid, sulfuric acid, hydrochloric acid, formic acid and the like, with methanesulfonic acid and trifluoroacetic acid being preferred and methanesulfonic acid being most preferred. The reaction is carried out either without a solvent or with a suitable solvent, such as toluene, tetrahydrofuran, or toluene/tetrahydrofuran mixtures. The use of a solvent is preferred. When a solvent is used, toluene is preferred. The reaction is carried out at a temperature of from about 20° C. to about 60° C., with 40° C. to 50° C. being preferred. The product can be isolated by extraction to give the product as a solution. The product can be purified by techniques well known in the art, such as evaporation, and recrystallization. The product can also be extracted into water using an appropriate base and used as an aqueous solution of its salt in the next step without purification.

In Scheme A, step 5, an alkyl 2-(difluoromethyl)-2-carboxy- 4-(p-fluorophenyl)butyrate is contacted with an appropriate base to give an alkyl (E)-2-(fluoromethylene)-4-(p-fluorophenyl)butyrate.

An appropriate base is any base capable of removing the carboxy proton of an alkyl 2-(difluoromethyl)-2-carboxy-4-(p-fluorophenyl)butyrate in a decarboxylative elimination reaction to give (E)-2-(fluoromethylene)-4-(p-fluorophenyl)butyrate. Appropriate bases include triethylamine, sodium bicarbonate, sodium carbonate, sodium hydroxide, potassium hydroxide, and the like.

For example, an alkyl 2-(difluoromethyl)-2-carboxy-4-(p-fluorophenyl)butyrate is contacted with an essentially equimolar amount of an appropriate base. The reaction is carried out in a suitable solvent, such as tetrahydrofuran, toluene, water or tetrahydrofuran/water mixtures with tetrahydrofuran/water mixtures being preferred and tetrahydrofuran/water mixtures of around 1 to 1 by weight being most preferred. The reaction is carried out at a temperature of from about −10° C. to about 40° C., with 0° C. to 25° C. being preferred. The reaction generally requires from 1 to 6 hours. The product can be isolated by techniques well known in the art, such as extraction and evaporation. The product can also be purified by techniques well known in the art, such as chromatography and distillation.

In Scheme A, step 6, an alkyl (E)-2-(fluoromethylene)4-(p-fluorophenyl)butyrate is contacted with an appropriate reducing agent to give (E)-2-(fluoromethylene)-4-(p-fluorophenyl)butan-1-ol.

An appropriate reducing agent is one that is capable of reducing the ester group of an alkyl (E)-2-(fluoromethylene)- 4-(p-fluorophenyl)butyrate in the presence of the fluoromethylene group. Appropriate reducing agents include sodium borohydride, lithium borohydride, potassium tri-sec-butylborohydride, 9-borabicyclo[3.3.1]nonane, lithium aluminum hydride, diisobutylaluminum hydride, and the like, with diisobutylaluminum hydride being preferred.

For example, an alkyl (E)-2-(fluoromethylene)-4-(p-fluorophenyl)butyrate is contacted with about 2.0 to about 3.0 equivalents of an appropriate reducing agent. The reaction is carried out in a suitable solvent, such as hexane, cyclohexane, dichloromethane, tetrahydrofuran, or toluene, with tetrahydrofuran and toluene being preferred and toluene being most preferred. The reaction is carried out by either adding a solution of an alkyl (E)-2-(fluoromethylene)- 4-(p-fluorophenyl)butyrate to a solution of an appropriate reducing agent or adding a solution of an appropriate reducing agent to a solution of an alkyl (E)-2- (fluoromethylene)-4-(p-fluorophenyl)butyrate. The addition is carried out at a temperature of from about −30° C. to about 10° C. The reaction is carried out at a temperature of from about 0° C. to about 30° C. The reaction generally requires 2 to 5 hours. The product can be isolated by quenching and extraction. The quench is carried out at a temperature of from about −15° C. to about 0° C. The product can be isolated as a solution by methods well known and appreciated in the art, such as extraction and evaporation. The product can be purified as is well known in the art by chromatography and distillation.

In Scheme A, step 7, (E)-2-(fluoromethylene)-4-(p-fluorophenyl)butan- 1-ol is contacted with an appropriate halogenating agent to give a (E)-1-halo-2-(fluoromethylene)-4-(p-fluorophenyl)butane.

An appropriate halogenating agent is one that converts a hydroxyl group to a halo group and does not cause the degradation of the the starting material or the product. Appropriate halogenating reagents are well known in the art and include, phosphorous trichloride, phosphorous tribromide, thionyl chloride, thionyl bromide, oxalyl chloride, the Vilsmeier reagent, and the like. As is well known in the art, the Vilsmeier reagent can be formed utilizing either a catalytic amount or slight molar excess of N,N-dimethylformamide and various chlorinating agents, such as phosphoryl chloride, phosgene, phosphorous trichloride, and oxalyl chloride.

For example, (E)-2-(fluoromethylene)-4-(p-fluorophenyl)butan- 1-ol is contacted with 1.0 to 1.5 molar equivalents of an appropriate halogenating agent. The reaction is carried out in a suitable solvent, such as dichloromethane and toluene. The reaction is carried out at a temperature of from about 20° C. to about 30° C. The reaction generally requires 4 to 24 hours. The product can be isolated by quenching with aqueous sodium chloride solution, extraction, and evaporation. The product can be purified as is well known in the art by chromatography and distillation.

In Scheme A, step 8, a (E)-1-halo-2-(fluoromethylene)4-(p-fluorophenyl)butane is contacted with an alkali metal salt of diformylamide to give (E)-N-(2-(fluoromethylene)-4-(p-fluorophenyl)butyl)-N-formyl formamide.

Examples of an alkali metal salt of diformylamide include sodium diformylamide, potassium diformylamide, and the like.

For example, a (E)-1-halo-2-(fluoromethylene)-4-(p-fluorophenyl)butane is contacted with 1.0 to 1.6 molar equivalents of an alkali metal salt of diformylamide. The reaction may be carried out in the presence of 0.05 to 0.5 molar equivalents of a suitable catalyst, such as sodium iodide or potassium iodide. The reaction is carried out in a suitable solvent, such as N-methylpyrrolidinone, N,N-dimethylformamide, acetonitrile, N-methylpyrrolidinone/acetonitrile mixtures, N,N-dimethylformamide/acetonitrile mixtures, or N,N-dimethylformamide/acetonitrile/toluene mixtures. The reaction is carried out at a temperature of from about 50° C. to about 90° C. The reaction generally requires 2 to 24 hours. The product can be isolated by quenching and extraction. The product can be purified as is well known in the art by chromatography and recrystallization.

In Scheme A, step 9, (E)-N-(2-(fluoromethylene)-4-(p-fluorophenyl)butyl)-N-formyl formamide is contacted with an appropriate hydrolysis agent to give (E)-1-amino-(2-fluoromethylene)- 4-(p-fluorophenyl)butane.

Appropriate hydrolysis agents are well known in the art including alkali metal hydroxides, such as lithium hydroxide, sodium hydroxide, potassium hydroxide and the like, and aqueous solutions of acids, such as hydrochloric acid, hydrobromic acid, and the like. For example, (E)-N-(2-(fluoromethylene)-4-(P-fluorophenyl)butyl)-N-formyl formamide is contacted with an appropriate hydrolysis agent. The reaction is carried out in a suitable solvent, such as water, methanol, ethanol, methanol/water mixtures, ethanol/water mixtures, and tetrahydrofuran/water mixtures. The reaction is carried out at a temperature of from about 0° C. to about 150° C. The reaction generally requires 2 to 24 hours. The product can be isolated by quenching and extraction. The product can be purified as is well known in the art by chromatography and recrystallization.

In Scheme A, optional step 10, (E)-1-amino-2-(fluoromethylene)- 4-(p-fluorophenyl)butane is contacted, as is well known in the art, with an appropriate pharmaceutically acceptable acid to form a pharmaceutically acceptable acid addition salt.

Alkali metal salts of diformylamide, such as lithium diformylamide, sodium diformylamide, and potassium diformylamide are obtained as a granular solid by a novel crystallization process comprising the steps of: dissolving an alkali metal salt of diformylamide in a hydroxylic solvent and removing the hydroxylic solvent by distillation while adding an anti-solvent.

For example, an alkali metal salt of diformylamide is dissolved in a hydroxylic solvent, such as methanol, ethanol, propanol, isopropanol, butanol, and the like, with methanol being preferred. The volume of hydroxylic solvent used is not critical but should be kept to a minimal amount as a matter of convenience. The solution is heated to the temperature at which the hydroxylic solvent begins to distill and an anti-solvent is added to replace the hydroxylic solvent lost upon distillation. Examples of an anti-solvent include benzene, chlorobenzene, toluene, xylene, cyclohexane, hexane, cyclopentane, heptane, octane, isooctane, dichloromethane, acetonitrile, ethyl acetate, acetone, butanone, and tetrachloroethylene, with benzene, toluene, cyclohexane, and acetonitrile being preferred and toluene being most preferred. Distillation is continued until the alkali metal salt of diformylamide crystallizes. The volume of the solution being decreased as necessary to facilitate crystallization. The distillation may be continue until the hydroxylic solvent is substantially removed. The alkali metal salt of diformylamide is isolated by filtration and dried.

The foregoing processes are exemplified by the procedures given below. These procedures are understood to be illustrative only and are not intended to limit the scope of the invention in any way. As used in the procedures, the following terms have the meanings indicated: "g" refers to grams; "kg" refers to kilograms; "mol" refers to moles;

"mmol" refers to millimoles; "mL" refers to milliliters; "L" refers to liters; "bp" refers to boiling point; "mp" refers to melting point; "lb" refers to pounds; "° C." refers to degrees Celsius; "dec" refers to decomposition; "M" refers to molar; "psi" refers to pounds per square inch.

Preparation of (E)-2-(fluoromethylene)-4-p-fluorophenyl)butan-1-ol 1.1 Synthesis of t-butyl 4-(p-fluorophenyl)butyrate
Scheme A, step 1:

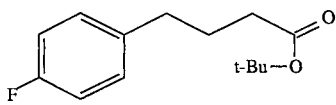

Combine 4-(p-fluorophenyl)butyric acid (51.4 g) and sulfuric acid (5.28 g, 98% Reagent ACS) in a Fisher-Porter bottle. Cool with a dry-ice bath to an internal temperature of between 0° C. and −20° C. Add isobutylene (54 g). Warm to ambient temperature. After 3 hours, cool in a dry-ice/acetone bath until the internal pressure differential of the vessel was 0 psi or less (about −20° C.). Carefully vent the Fisher-Porter bottle and add a cold solution of 5 M sodium hydroxide (51.5 g). Reseal the Fisher-Porter bottle and allow to warm to ambient temperature with vigorous stirring. Vent the Fisher-Porter vessel to remove excess isobutylene. Extract the reaction mixture with toluene (75 g). Separate the organic layer and extract with a saturated sodium bicarbonate solution (77 g). Evaporate in vacuo to obtain the title compound. $^1$H NMR (CDCl$_3$, 300 MHz) δ1.45 (s, 9H), 1.84 (m, 2H) 2.23 (t, J=7.5 Hz, 2H), 2.61 (t, J=7.5 Hz, 2H), 6.96 (m, 2H), 7.13 (m, 2H).

2.1 Synthesis of ethyl 2-(t-butoxycarbonyl)-4-(P-fluorophenyl)butyrate
Scheme A, step 2:

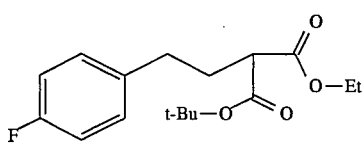

Prepare a solution of lithium diisopropylamide from diisopropylamine (22.74 g) and 1.6M n-butyl lithium (143.7 mL) in tetrahydrofuran (200 mL). Cool to −78° C. Slowly add t-butyl 4-p-(fluorophenyl)butyrate (26.76 g) as a solution in tetrahydrofuran (100 mL). After 1 hour, add ethyl chloroformate (12.19 g) as a solution in tetrahydrofuran (100 mL). After 24 hours, pour the reaction mixture into water, neutralize with dilute aqueous hydrochloric acid solution. Extract with diethyl ether. Dry the organic layer over MgSO$_4$, filter, and evaporate in vacuo to give the title compound.

3.1 Synthesis of ethyl 2-(difluoromethyl)-2-(t-butoxycarbonyl)-4-(p-fluorophenyl)butyrate
Scheme A, step 3:

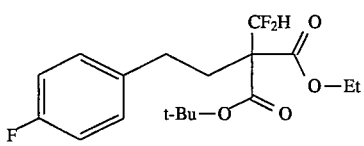

Combine ethyl 2-(t-butoxycarbonyl)-4-(p-fluorophenyl)butyrate (32.14 g) and sodium t-butoxide (19.81 g) in tetrahydrofuran (400 mL). Stir the mixture for 1 hour, then heat to 45° C. Add an excess of chlorodifluoromethane over about 15 minutes. After 1 hour under an atmosphere of chlorodifluoromethane, allow the temperature to fall to ambient. Pour the reaction mixture into water/brine. Extract with diethyl ether. Dry the organic layer over MgSO$_4$, filter, and evaporate in vacuo to give the title compound.

3.2 Synthesis of ethyl 2-(difluoromethyl),2-(t-butoxycarbonyl)- 4-(p-fluorophenyl)butyrate
Scheme A, step 2 and Scheme A, step 3:

Cool a tetrahydrofuran solution of sodium bis(trimethylsilyl)amide (545 kg, 2M, 877 mol) to −10° C. Slowly add, t-butyl 4-(p-fluorophenyl)butyrate (84.1 kg, 80% by weight in toluene, 353 mol). After 15 minutes, slowly add ethyl chloroformate (38.6 kg, 356 mol) at such a rate that the reaction temperature is maintained at or below −5° C. After 20 minutes, warm the reaction mixture to 40° C.–45° C. Seal the reaction vessel and add chlorodifluoromethane (38.15 kg, 445 mol) to the head space. After 1 hour, cool to 15° C. −20° C. and vent the reaction vessel. Add a solution of acetic acid (421 kg, 20% in water) and stir. After 30 minutes, separate the aqueous layer and evaporate the organic layer in vacuo to obtain a residue. Add toluene (45 kg) and evaporate in vacuo until the internal temperature of the reaction vessel is 55° C. to obtain the title compound as a toluene solution.

4.1 Synthesis of ethyl 2-(difluoromethyl)-2-carboxy-4-(P-fluorophenyl)butyrate
Scheme A, step 4:

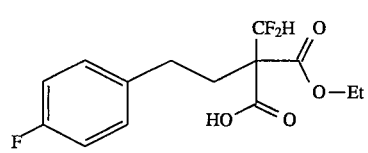

Add methanesulfonic acid (47.7 kg, 496 mol) to a toluene solution of ethyl 2-(difluoromethyl)-2-(t-butoxycarbonyl)-4-(p-fluorophenyl)butyrate as prepared in Example 3.1 at a temperature of 40° C. 50° C. After 3 to 6 hours, cool the reaction to ambient temperature. Add toluene (91 kg) and water (421 kg) and stir for 30 minutes. Separate the aqueous layer. Add to the organic layer a 20% by weight solution of sodium chloride in water (420 kg) and stir for 30 minutes. Separate the layers to give the title compound as a solution in toluene.

5.1 Synthesis of ethyl (E)-2-(fluoromethylene)-4-(p-fluorophenyl)butyrate
Scheme A, step 5:

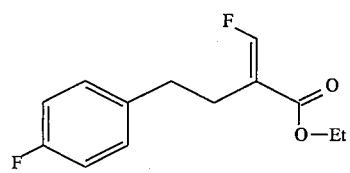

Cool to 0° C.–10° C. a toluene solution of ethyl 2-(difluoromethyl)- 2-carboxy-4-(p-fluorophenyl)butyrate as prepared in Example 4.1. Add water (396 kg) and a 50% by weight aqueous solution of sodium hydroxide. Stir for 30 minutes. Separate the aqueous layer and cool the aqueous layer to 0° C.–5° C. Add tetrahydrofuran (421 kg). Stir for 1 hour at 0° C. and then warm to 25° C. and stir for 3 hours. Separate the aqueous layer. Evaporate the organic layer in vacuo at a temperature of 40° C.–50° C. The evaporation is continued until tetrahydrofuran no longer comes over and then toluene is added. Evaporate in vacuo until there is no longer water visible in the condensate. Concentrate in vacuo to give the title compound as a 80–90% by weight solution in toluene. An analytical sample prepared by evaporation of solvent gave ₁H NMR (CDCl₃, 300 MHz) δ1.28 (t, J=7.2 Hz 3H), 2.58 (m, 2H), 2.71 (m, 2H) 4.21 (q, J=7.2 Hz, 2H), 6.93 (m, 2H), 7.15 (m, 2H), 7.51 (d, J=81.9 Hz, 1H).

6.1 Synthesis of (E)-2-(fluoromethylene)-4-(p-fluorophenyl)butan-1-ol
Scheme A, step 6:

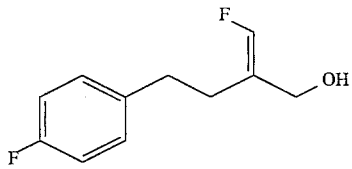

Combine ethyl (E)-2-(fluoromethylene)-4-(p-fluorophenyl)butyrate (1.5 g, 6.24 mmol) and toluene (5 mL). Cool to −15° C. Add dropwise, a solution of diisobutylaluminum hydride (10.4 mL, 1.5M in toluene, 15.6 mmol). Warm to ambient temperature. After 18 hours, cool to 0° C. With vigorous stirring add sequentially, methanol (15 mL), an aqueous 5M hydrochloric acid solution (25 mL), and water (35 mL). When gas evolution ceases, extract with toluene. Separate the layers and evaporate organic layer in vacuo to give the title compound. ¹H NMR (CDCl₃, 300 MHz) δ 2.28 (s, 1H), 2.45 (m, 2H), 2.72 (m, 2H) 3.91 (d, J=3 Hz, 2H), 6.57 (d, J=87 Hz, 1H), 6.96 (m, 2H), 7.13 (m, 2H).

6.2 Synthesis of (E)-2-(fluoromethylene)-4-(p-fluorophenyl)butan-1-ol
Scheme A, step 6:

Cool to 0° C. a solution of diisobutylaluminum hydride (7.64 kg, 25% by weight in toluene, 13.42 mol). Add a solution of ethyl (E)-2-(fluoromethylene)-4-(p-fluorophenyl)butyrate (1.74 kg, 74.1% by weight in toluene, 5.37 mol) at such a rate that the temperature of the reaction mixture does not rise above 20° C. After the addition is complete, warm to ambient temperature. After 2 hours, cool to 0° C. Slowly, add methanol (7.73 kg) at such a rate that the temperature of the reaction mixture does not rise above 15° C. Cool to 0° C. Slowly, add water (7.96 kg) at such a rate that the temperature of the reaction mixture does not rise above 20° C. Add a concentrated aqueous solution of hydrochloric acid (7.59 kg). Warm to ambient temperature. Separate the organic layer and dry azeotropically by distillation in vacuo until the volume of the organic layer is about one half of its original volume to give the title compound as a solution in toluene.

Preparation of (E)-1-amino-2-(fluoromethylene)-4-(p-fluorophenyl)butane 7.1 Synthesis of (E)-1-bromo-2-(fluoromethylene)-4-(p-fluorophenyl)butane
Scheme A, step 7:

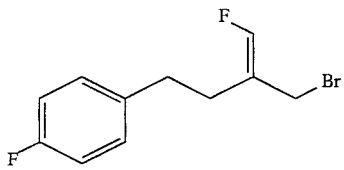

Combine (E)-2-(fluoromethylene)-4-(p-fluorophenyl)butan1-ol (4.0 g, 20.2 mmol) and toluene (10 mL). Cool to about −5° C. Add dropwise, a solution of phosphorous tribromide (1.8 g, 6.65 mmol) in toluene (5 mL). After 1 hour, warm to ambient temperature. After 18 hours, cool to 0° C. and then add saturated sodium bicarbonate solution (50 mL). Separate the layers and extract the aqueous layer 3 times with toluene (40 mL). Extract the combined organic layers with a saturated aqueous sodium chloride solution, dry over Na₂SO₄, filter, and evaporate in vacuo to give the title compound.

7.2.1 Synthesis of (E)-1-chloro-2-(fluoromethylene)-4-(p-fluorophenyl)butane
Scheme A, step 7:

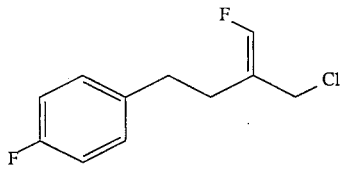

Combine oxalyl chloride (2.71 g, 21.4 mmol) and toluene (20 mL). Cool to 0° C. Add N,N-dimethylformamide (1.62 g, 22.2 mmol) as a solution in toluene (2 mL). Warm to ambient temperature. After 10 minutes, cool to 0° C. Add (E)-2(fluoromethylene)- 4-(p-fluorophenyl)butan-1-ol (4.0 g, 20.2 mmol) Warm to ambient temperature. After 18 hours, pour the reaction mixture into a saturated sodium chloride solution (100 mL). Extract the aqueous layer 3 times with toluene. Dry the combined organic layers over Na₂SO₄, filter, and evaporate in vacuo to give the title compound. ¹H NMR (CDCl₃, 300 MHz) δ2.52 (m, 2H), 2.75 (m, 2H), 3.91 (d, J=6 Hz, 2H), 6.65 (d, J=82.5 Hz, 1H), 6.95 (m, 2H), 7.15 (m, 2H).

7.2.2 Synthesis of (E)-1-chloro-2-(fluoromethylene)-4-(p-fluorophenyl)butane
Scheme A, step 7:

Combine oxalyl chloride (25.2 g, 0.198 mol) and toluene (200 mL). Cool to −5° C. Add N,N-dimethylformamide (15.0 g, 0.21 mol) as a solution in toluene (20 mL). Warm to 25° C. After 30 minutes, add a solution of (E)-2-(fluoromethylene)- 4-(p-fluorophenyl)butan-1-ol (24.7 g, 30% by weight in toluene, 0.124 mol). After 18 hours, add water (500 mL) and stir for 30 minutes. Separate the organic layer, dry over Na₂SO₄, filter, and evaporate in vacuo to give the title compound.

8.1.1 Synthesis of (E)-N-(2-(fluoromethylene)-4-(p-fluorophenyl)butyl)-N-formyl formamide
Scheme A, step 8:

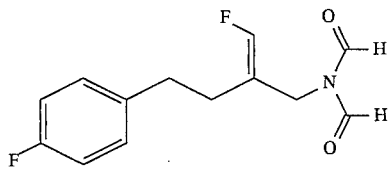

Combine sodium diformylamide (28.8 g, 0.31 mol), acetonitrile (360 g), and N,N-dimethylformamide (48 g). Add (E)-1-chloro-2-(fluoromethylene)-4-(p-fluorophenyl)butane (50.6 g, 0.23 mol). Heat to reflux. After 5 hours, cool to ambient temperature. Add water (466 g) and stir for 15 minutes. After 30 minutes, the aqueous layer is removed. Evaporate the organic layer in vacuo to give the title compound. ¹H NMR (CDCl₃, 300 MHz) δ2.28 (m, 2H), 2.72 (m, 2H), 4.07 (d , J=3Hz, 2H), 6.74 (d, J=81Hz, 1H), 6.94 (m, 2H), 7.13 (m, 2H), 8.73 (s, 2H).

8.1.2 Synthesis of (E)-N-(2-(fluoromethylene)-4-(p-fluorophenyl)butyl)-N-formyl formamide
Scheme A, step 8:

Combine sodium diformylamide (70 lb) and acetonitrile (903 lb). With agitation, add N,N-dimethylformamide (119 lb). Add a solution of (E)-1-chloro-2-(fluoromethylene)-4-(p-fluorophenyl)butane (126 lb) in toluene. Warm to 80° C.

After 6 hours, add a 10% by weight solution of sodium chloride in water (1168 lb). Agitate for 15 minutes, separate the layers. Remove the organic layer to give the title compound as a solution in acetonitrile/N,N-dimethylformamide.

9.1.1 Synthesis of (E)-1-amino-2-(fluoromethylene)-4-(p-fluorophenyl)butane hydrochloride salt
Scheme A, step 9 and Scheme A, optional step 10:

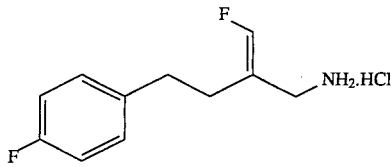

Combine (E)-N-(2-(fluoromethylene)-4-(p-fluorophenyl)butyl)-N-formyl formamide (8.0 g, 32.7 mmol), ethanol (19.9 g), water (29.8 g), and aqueous 12M hydrochloric acid solution (13.1 g). Heat to reflux. After 1 hour, add toluene (29.8 g). Cool to 25° C. Separate the layers. Distill the aqueous layer until the volume is reduced by about two thirds. Cool to 50° C. Add concentrated aqueous hydrochloric acid solution (50 g). Cool to −5° C., filter, rinse with toluene, and dry in vacuo at 60° C. to give a solid. Recrystallize the solid from isopropyl acetate, filter, and dry in vacuo at 43° C. to give the title compound: mp 130°–131.5° C. 1H NMR (D20, 300 MHz) 8 2.50 (m, 2H), 2.79 (m, 2H), 3.47 (d, J=3.0 Hz, 2H), 6.80 (d, J=81.9 Hz, 1H), 7.09 (m, 2H), 7.28 (m, 2H).

9.1.2 Synthesis of (E)-1-amino-2-(fluoromethylene)-4-(p-fluorophenyl)butane hydrochloride salt
Scheme A, step 9 and Scheme A, optional step 10:

Evaporate a acetonitrile/N,N-dimethylformamide solution of crude (E) -N-(2-(fluoromethylene)-4-(p-fluorophenyl)butyl) -N-formyl formamide as prepared in Example 8.1. 2 (1951.5 lb, 12.9% by weight of (E)-N-(2( fluoromethylene)-4-(p-fluorophenyl)butyl)-N-formyl formamide) Combine (E)-N-(2-(fluoromethylene)-4-(p-fluorophenyl)butyl)-N-formyl formamide (252 lb) obtained by evaporation above, ethanol (504 lb), water (760), and aqueous 12M hydrochloric acid solution (328 lb). Heat to 81° C.–89° C. After 2.5 hour, add toluene (784 lb) stir and separate the layers. Evaporate the aqueous layer in vacuo until about 80–110 gallons of liquid remain. Add concentrated aqueous hydrochloric acid solution (1678 lb). Cool to 0° C. over 6 hours, to give a solid. Collect the solid by filtration, rinse with toluene, and dry in vacuo at 60° C. to give the title compound.

Process for crystallizing alkali metal salts of diformylamide
10.1 Synthesis and Crystallization of sodium diformylamide
Combine a solution of sodium methoxide (801.6 g, 25% by weight in methanol, 3.71 mol) and formamide (334 g, 7.42 mol). After 1 hour, heat to reflux. Remove methanolic ammonia by distillation. Continue the distillation, add toluene (800 g) dropwise at a rate approximately equal to the rate of solvent loss. Distill until the temperature of the still head reaches 110° C. Cool to ambient temperature, filter and dry to give sodium diformylamide as a granular solid: mp 185–190 (dec).

10.2 Crystallization of sodium diformylamide
Combine sodium diformylamide (352.5 g, 3.71 mol) and methanol (290 g) in a suitable distillation apparatus. Heat until methanol begins to distill. As the distillation proceeds, add toluene (800 g) dropwise at a rate approximately equal to the rate of solvent loss. Distill until the temperature of the still head reaches 110° C. Cool to ambient temperature, filter and dry to give sodium diformylamide.

10.3 Crystallization of potassium diformylamide
Combine potassium diformylamide (392 g, 3.5 mol) and ethanol (400 g) in a suitable distillation apparatus. Heat until ethanol begins to distill. As the distillation proceeds, add toluene (1000 g) dropwise at a rate approximately equal to the rate of solvent loss. Distill until the temperature of the still head reaches 110° C. Cool to ambient temperature, filter and dry to give potassium diformylamide.

What is claimed is:

1. The compound (E)-1-chloro-2-(fluoromethylene)-4-(p-fluorophenyl)butane.

2. The compound (E)-1-bromo-2-(fluoromethylene)-4-(p-fluorophenyl)butane.

\* \* \* \* \*